United States Patent
Dinjus et al.

(10) Patent No.: US 6,518,446 B1
(45) Date of Patent: Feb. 11, 2003

(54) METHOD FOR PRODUCING FORMOXYSILANE

(75) Inventors: Eckhard Dinjus, Leimersheim (DE); Stephan Pitter, Stutensee (DE); Achim Jansen, Jena (DE)

(73) Assignee: Forschungszentrum Karlsruhe GmbH (DE)

( * ) Notice: Subject to any disclaimer, the term of this patent is extended or adjusted under 35 U.S.C. 154(b) by 0 days.

(21) Appl. No.: 09/936,716

(22) PCT Filed: Mar. 6, 2000

(86) PCT No.: PCT/EP00/01933

§ 371 (c)(1),
(2), (4) Date: Jan. 24, 2002

(87) PCT Pub. No.: WO00/55163

PCT Pub. Date: Sep. 21, 2000

(30) Foreign Application Priority Data

Mar. 15, 1999 (DE) .......................... 199 11 616

(51) Int. Cl.⁷ .................................................. C07F 7/08
(52) U.S. Cl. ...................................................... 556/442
(58) Field of Search .......................................... 556/442

(56) References Cited

U.S. PATENT DOCUMENTS 5,013,854 A * 5/1991 Bunnell .................. 556/442 X
6,060,620 A * 5/2000 Tachikawa .................. 556/442

OTHER PUBLICATIONS

Jansen et al., "trans–[RuIICl(MeCN)5][RUIIICl4(MeCN)2]:A Reactive Intermediate in the Homogeneous Catalyzed Hydrosilylation of Carbon Dioxide", Organometallics, Bd. 19, Nr. 2 Jan. 24, 2000, pp. 135–138.*

* cited by examiner

*Primary Examiner*—Paul F. Shaver
(74) *Attorney, Agent, or Firm*—Venable; Robert Kinberg

(57) ABSTRACT

The invention relates to a method for producing formoxysilane. A silane of the formula $R_nSiH_{4-n}$, wherein R is an organic or inorganic substituent and n=0, 1, 2 or 3, is converted with carbon dioxide in a solvent in the presence of a catalyst consisting of a compound of a transitional metal pertaining to the subgroup VIIIb of the periodic system. The aim of the invention is to find a catalyst for the method mentioned above. The catalyst should be more simple, easy to produce and thus more cost-effective, easily available in large quantities and being provided with high activity and product selectivity. To this end, a halide of the transitional metal or a compound of the transitional metal are used as catalyst. Said compound is produced by converting a halide of the transitional metal with a nitrile in the presence of the silane of the formula $R_nSiH_{4-n}$.

4 Claims, No Drawings

METHOD FOR PRODUCING FORMOXYSILANE

The invention relates to a method for producing a formoxysilane in accordance with the preamble to claim 1 or 2.

Acyloxysilane with the general formula $R_nSi[O-C(O)R']_{4-n}$, in which R and R' represent an organic residue or hydrogen and n=0, 1, 2 or 3, form a class of compounds of high technical importance. The silylesters of the acetic acid (R'=CH$_3$—) are used on an industrial scale for the production of cross-linked RTV (room temperature vulcanization) silicones. The cross-linking of acyloxysilanes is started because the silylester group is easily hydrolyzed. With sealing materials, for example used for the pointing of joints in the sanitary region, the normal humidity in the air is sufficient to start a cross-linking (Ullman's Encyclopedia of Industrial Chemistry, 4$^{th}$ ed., Vol. 22, 77–80 and 119–120). Formoxysilane (R'=H) in addition has a potential for the production of defined SiO$_2$ layers on various substrates, which is achieved through CVD (chemical vapor deposition) (EP 0778278 A).

A method of the aforementioned type follows from the Publication by H. Koinuma, F. Kawakami, H. Kato, H. Hirai, J. Chem. Soc. Chem. Comm., 1981, 213; and G. S üss-Fink; J. Reiner, J. Organomet. Chem., 221, 1981, C36.

With this method, a silane is hydrolyzed with carbon dioxide in a solvent and in the presence of a homogeneous catalyst:

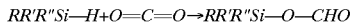

RR'R"Si—H+O=C=O→RR'R"Si—O—CHO

Complex compounds of palladium and ruthenium function as homogeneous catalyst. Up to 275 catalytic cycles per mol equivalent of the catalyst are achieved for the generating of formoxysilanes from the conversion of silanes of the type RR'R"SiH (R, R', R"=CH$_3$—, C$_2$H$_5$—, —OCH$_3$), wherein the reaction conditions are 60° C. up to 120° C. reaction temperature, 20 h to 60 h reaction time as well as 30 to 50 bar CO$_2$ pressure. A re-processing and reuse of the catalysts is not mentioned.

Hydrolyzing carbon dioxide has the following advantages: carbon dioxide is non-toxic and is therefore quite harmless ecologically. In addition, it has no competition and is cheap as C$_1$ substrate. Economic advantages can be achieved in particular if a more cost-effective catalyst is found, which can be recycled if necessary.

Thus, it is the object of the invention to find a simpler, easier to produce and thus most cost-effective catalyst for the aforementioned type of method, which can be obtained on a large scale and has a high activity and product selectivity. With a suitable realization of the method, the catalyst should be recyclable.

This object is solved with the catalyst specified in the characterizing section of claims 1 or 2. Preferred embodiments of the initially mentioned methods are listed in the additional claims.

Formoxysilanes with the general formula $R_nSi[O-C(O)H]_{4-n}$, can be produced with the method according to the invention. R represents an organic or inorganic substituent, preferably an alkyl, alkenyl, aryl, aryloxy group or a halide or R$^1$R$^2$R$^3$SiO residue, wherein R$^1$, R$^2$ and R$^3$ is an additional organic or inorganic substituent. The index n can assume whole number values of 0 to 3, preferably 2 or 3.

According to the invention, ruthenium chloride (RuCl$_3$·xH$_2$O) is used in a first embodiment as catalyst. The starting material for this embodiment is an acyloxysilane in a solvent, to which the catalyst is added. The carbon dioxide is then pressed on. The reaction temperature should be in the range of 20° C. to 120° C. Pressures ranging form 1 bar to 200 bar are suitable for the carbon dioxide partial pressure and the reaction time is between 0.5 h and 50 h.

In a second embodiment of the invention, a compound of the transitional metal is used as the catalyst, which is formed through conversion of a halide of the transitional metal with a nitrile in the presence of the silane with formula $R_nSiH_{4-n}$. Thus, we are dealing with a pre-formed catalyst, consisting of a silane and one of the above-mentioned catalysts, preferably ruthenium chloride. The pre-forming preferably occurs without pressure. The silane and the catalyst, preferably RuCl3·xH2O can be dissolved for this in a solvent, for example acetone nitrile, and the solvent can be heated to reflux. A catalytically especially effective compound is generated during the pre-forming, which has the empirical formula C$_{24}$H$_{36}$Cl$_6$N$_{12}$Ru$_3$.

The pre-formed catalyst has the advantage that the temperature for the subsequent hydrolyzing operation, carried out at the partial pressure specified for carbon, can be selected to be considerably lower than that for the first embodiment.

With the second embodiment, a solution of the silane in a solvent can thus be used as starting material, to which the catalyst, in particular with ruthenium chloride, is added at the specified temperature. Once the solution has been heated to reflux, the carbon dioxide is pressed on without further cleaning and the reactor is heated to a temperature of 30° C. to 100° C. while stirring the reactor content. The reaction time generally is between 1 and 40 hours. The reactor is subsequently cooled down, if necessary the pressure relieved, and the reaction product is isolated through distillation, rectification or extraction.

Suitable solvents are nitrites, benzenoid aromatic compounds, halogenated hydrocarbons or mixtures thereof Higher-boiling nitrites are preferably used as solvent for the lower-boiling products. The advantage is that the resulting products can be distilled directly out of the reaction mixture and the residue, which contains the catalyst, can be used for additional conversions.

Between 1/10 and 1/5000 equivalents of the catalyst are preferably used per equivalent Si—H-groups, referred to equivalents of the active metal.

The product yields with the formula $R_nsi[O-C(o)H]_{4-n}$ in particular depend on the type of catalyst used and the substituents R of the silane. In the most favorable case, nearly quantitative yields are obtained, relative to the silane used. The TON (turnover number, or number of conversions per catalyst atom) reaches up to 5000 $mol_{acyloxysilane}/mol_{active\ metal}$ per batch with a TOF (turn over frequency, number of conversions per hour) of up to 500 $h^{-1}$. Multifunctional products (n=0, 1, 2) can be used as cross-linking components for silicon materials owing to their capacity to easily hydrolyze.

In the following, the invention is explained in further detail with the aid of exemplary embodiments.

Representation of a pre-formed catalyst.

A solution of 1.09 g dimethylphenylsilane and 1.98 g $RuCl_3 \cdot xH_2O$ (x is computed from the analyzed water content and has the value 2.23 for the feed material used for these experiments) is heated for 4 h to reflux in 50 ml acetone nitrile. The resulting suspension is hot-filtrated and the solid material obtained is washed twice with respectively 6 ml acetone nitrile, diethyl ether and pentane. Following the drying in a high vacuum (24 h), 2.13 g (79%) of an orange-colored solid material with the empirical formula $C_{24}H_{36}Cl_6N_{12}Ru_3$ is obtained.

Hydrolyzing of Carbon Dioxide
General Work Specifications (GWS) 1

Once the pre-formed catalyst according to the above specifications is placed into the reactor chamber of an autoclave, this autoclave is closed and secured. Subsequently, the acetone nitrile and the silane are added and the required amount of carbon dioxide pressed on. Upon completion of the reaction according to the reaction conditions (Table 2), the autoclave is relaxed via a bubble counter, the reaction solution removed and, if necessary, filtered. The solvent is removed in the vacuum (8 mbar) at 30° C. and the product obtained from the residue through distillation.

through distillation, wherein the catalyst remains in the less volatile solvent.

The $^{29}Si$—NMR displacements of the reaction products ($CDCl_3$) are listed in Table 1. The experimental conditions are shown in Table 2. The reaction parameters for the synthesis of formoxysilane through catalytic hydrolyzing of carbon dioxide are listed in Table 2.

TABLE 1

$^{29}$Si-NMR displacements ($CDCl_3$) of formoxysilanes, produced through the catalytic hydrolyzing of $CO_2$ (see Table 2).

| formyloxysilane[1] | $\delta^{29}$Si-NMR [ppm] |
|---|---|
| HCOO—SiEt$_3$ | 27.6 |
| HCOO—SiHex$_3$ | 24.9 |
| HCOO—Si(CH$_2$Ph)Me$_2$ | 22.0 |
| HCOO—SiMe$_2$Ph | 14.2 |
| HCOO—SiMePh$_2$ | 2.5 |
| HCOO—Si(CH$_2$—CH=CH$_2$)Me$_2$ | 21.8 |
| (HCOO)$_2$SiPh$_2$ | −16.8 |
| HCOOSiMe$_2$OMe$_2$SiOOCH | −6.0 |

[1]Note:
This is a typing mistake and should read "formoxysilane."

TABLE 2

Reaction parameters for the synthesis of formoxysilanes, produced through catalytically hydrolyzing $CO_2$.

| | | silane | | catalyst | | solvent | | $CO_2$ | | | | Yield |
|---|---|---|---|---|---|---|---|---|---|---|---|---|
| No. | AAV | | m[g] | type | m[g] | | V[m] | m[g] | t[h] | T[° C.] | p[bar] | % |
| 1 | 2 | HSiEt$_3$ | 4.65 | Ru$_2$(CH$_3$CH)$_7$Cl$_5$ | 0.0269 | Ph(CH$_2$)$_2$CN | 30 | 3.5 | 20 | 100 | 16 | 91 |
| 2 | 1 | HSiHex$_3$ | 11.38 | RuCl$_3 \cdot$xH$_2$O | 0.0990 | CH$_3$CN | 30 | 26.4 | 62 | 100 | 81 | 84 |
| 3 | 1 | HSi(CH$_2$Ph)Me$_2$ | 6.01 | Ru$_2$(CH$_3$CN)$_7$CL$_5$ | 0.0269 | CH$_3$CN | 30 | 3.5 | 20 | 80 | 10 | 90 |
| 4 | 1 | HSiMe$_2$Ph | 5.45 | Ru$_2$(CH$_3$CN)$_7$CL$_5$ | 0.0269 | CH$_3$CN | 30 | 3.5 | 4 | 60 | 10 | 95 |
| 5 | 1 | HSiMe$_2$Ph[1] | 5.45 | Ru$_2$(CH$_3$CN)$_7$CL$_5$ | 0.0269 | CH$_3$CN | 30 | 3.5 | 20 | 40 | 8 | 22 |
| 6 | 1 | HSiMe$_2$Ph$_2$ | 7.93 | RuCl$_3 \cdot$xH$_2$O | 0.0198 | CH$_3$CN | 30 | 3.5 | 20 | 100 | 12 | 88 |
| 7 | 2 | HSi(CH$_2$—CH=CH$_2$)Me$_2$ | 3.00 | Ru$_2$(CH$_3$CN)$_7$CL$_5$ | 0.1006 | Ph(CH$_2$)$_2$CN | 30 | 2.6 | 20 | 60 | 14 | 48 |
| 8 | 1 | H$_2$SiPh$_2$ | 3.69 | Ru$_2$(CH$_3$CN)$_7$CL$_5$ | 0.1345 | CH$_3$CN | 30 | 26.4 | 20 | 70 | 62 | 89 |
| 9 | 1 | HSiMe$_2$OMe$_2$SiH | 2.69 | Ru$_2$(CH$_3$CN)$_7$CL$_5$ | 0.1345 | CH$_3$CN | 30 | 3.5 | 4 | 70 | 11 | 74 |

[1]Repeat of experiment from the previous line. This is shown such that the pre-formed catalyst can be used with a lower process temperature. For a complete conversion of the silane, the reaction time must be changed.

General Work Specifications (GWS) 2

Once the pre-formed catalyst according to the above specifications is placed into the reactor chamber of an autoclave, this autoclave is closed and secured. Subsequently, 3-phenylpropionitrile and silane are added and the necessary amount of carbon dioxide is pressed on. Upon completion of the reaction according to the reaction conditions (Table 2), the autoclave is relaxed via a bubble counter, the reaction solution removed and, if necessary, filtered. The product is obtained from the reaction solution

What is claimed is:

1. A method for producing a formoxysilane comprising converting a silane having the formula $R_nSiH_{4−n}$, where R is an organic or inorganic substituent and n is 0,1,2, or 3, in a solvent in the presence of a ruthenium tricholride catalyst, prepared by reacting ruthenium trichoride with a nitrile in the presence of the silane, with carbon dioxide.

2. A method for producing formoxysilane comprising converting a silane having the formula $R_nSiH_{4−n}$, where R is an organic or inorganic substituent and n is 0,1,2, or 3, in a solvent in the presence of a subgroup VIIIb metal containing catalyst with carbon dioxide, wherein the catalyst is formed through conversion of a halide of the transitional metal with a nitrile in the presence of the silane with the formula $R_nSiH_{4-n}$.

3. The method according to claim 1 or 2 wherein 1/10 to 1/5000 equivalents of the catalyst are used per equivalent of the Si—H group, as referred to the equivalent of the transitional metal.

4. The method according to claim 1 or 2 wherein the solvent is a nitrile, a benzenoid aromatic or a halogenated hydrocarbon.

* * * * *